United States Patent [19]

Rotgerink et al.

[11] Patent Number: 5,849,657
[45] Date of Patent: Dec. 15, 1998

[54] CATALYST FOR THE DEHYDROGENATION OF $C_6$-$C_{15}$ PARAFFINS AND TO A PROCESS FOR MAKING SUCH CATALYSTS

[75] Inventors: Hans Lansink Rotgerink, Glattbach; Thomas Tacke, Friedrichsdorf; Reinhold Brand, Gelnhausen; Peter Panster, Rodenbach, all of Germany

[73] Assignee: Degussa Aktiengesellschaft, Frankfurt am Main, Germany

[21] Appl. No.: 560,096

[22] Filed: Nov. 17, 1995

[30] Foreign Application Priority Data

Nov. 29, 1994 [DE] Germany ............. 44 42 327.6

[51] Int. Cl.⁶ ................................. B01J 27/045
[52] U.S. Cl. ............... 502/223; 502/230; 502/334; 502/339; 502/349; 502/352
[58] Field of Search .............. 502/339, 328, 502/334, 349, 352, 223, 230

[56] References Cited

U.S. PATENT DOCUMENTS

| | | | |
|---|---|---|---|
| 3,745,112 | 7/1973 | Rausch | 208/139 |
| 3,892,657 | 7/1975 | Wilhelm | 208/139 |
| 3,998,900 | 12/1976 | Wilhelm | 260/668 |
| 4,486,547 | 12/1984 | Imai et al. | 502/223 |
| 4,886,928 | 12/1989 | Imai et al. | 585/660 |
| 4,964,975 | 10/1990 | Chao et al. | 208/139 |

FOREIGN PATENT DOCUMENTS 753072  12/1970  Belgium .

OTHER PUBLICATIONS

European Search Report dated Oct. 4, 1996.

*Primary Examiner*—Shrive Beck
*Assistant Examiner*—Timothy Meeks
*Attorney, Agent, or Firm*—Beveridge, DeGrandi, Weilacher & Young, L.L.P.

[57] ABSTRACT

A catalyst for the dehydrogenation of $C6_6$–$C_{15}$ paraffins is disclosed. The catalyst contains, on a support, at least one platinum group component, at least one promoter component from the group tin, germanium and lead, and at least one additional modifier. The additional modifier contains at least one alkaline earth metal. The stability of the catalyst is essentially higher than that achieved by conventional use of an alkali metal.

21 Claims, No Drawings

CATALYST FOR THE DEHYDROGENATION OF $C_6$-$C_{15}$ PARAFFINS AND TO A PROCESS FOR MAKING SUCH CATALYSTS

INTRODUCTION AND BACKGROUND

The present invention relates to a catalyst for the dehydrogenation of $C_6$–$C_{15}$ paraffins and to a process for making such catalysts.

The dehydrogenation of hydrocarbons and in particular of paraffins is performed on an industrial scale. The dehydrogenated products are required for the production of a variety of chemical compounds such as, for example, detergents, components for gasoline, and pharmaceutical products. The dehydrogenation of normal paraffins with 6–15 carbon atoms to give the corresponding monoolefins is of particular importance for the production of detergents. Monoolefins are used for alkylating aromatic compounds such as, for example, benzene, to give the corresponding linear alkylbenzenes.

Dehydrogenation of paraffins is performed in the presence of a suitable catalyst under dehydrogenation conditions. The paraffins may make contact with the catalyst in a fixed bed, in a fluidized bed or in a moving bed. A fixed bed catalyst system is preferably used where the reactant to be dehydrogenated is first preheated to the required reaction temperature and then passed over the fixed bed catalyst. Hydrocarbons are preferably dehydrogenated in the vapour phase. The temperatures required for this are in the range between 300° and 900° C.

Catalysts used for dehydrogenation on an industrial scale contain platinum on aluminum oxide as support. The catalysts generally also contain several promoters, for example tin and/or indium. When dehydrogenating normal paraffins the objective is to produce straight-chain monoolefins. Therefore side reactions or consecutive reactions to give isoolefins, isoparaffins or alkylated aromatic compounds should be avoided. In practice, these unwanted reactions are suppressed by adding an alkali metal which modifies the catalytic activity in an appropriate manner.

U.S. Pat. No. 4,486,547 (which is incorporated by reference in its entirety) discloses, for example, a catalyst composition which contains a platinum group component, a tin component, an indium component, and an alkali metal or alkaline earth metal component on a porous support. In the examples, only catalysts with the alkali metal lithium are described.

Due to the additional indium component, the catalyst system in U.S. Pat. No. 4,486,547 exhibits greater stability of catalyst activity than comparable catalysts without indium. For industrial use of this type of catalyst system, however, further improvements in catalyst activity and in particular in long-term stability of the catalyst system are desirable.

SUMMARY OF THE INVENTION

An object of the present invention is to provide a catalyst system for the dehydrogenation of normal paraffins which is characterized by further improved long-term stability of the catalyst activity as compared with the systems known hitherto.

This object, and other objects, is achieved by a catalyst for the dehydrogenation of $C_6$–$C_{15}$ paraffins which contains, on an inorganic support, 0.01 to 5 wt. % of at least one platinum group metal, 0.01 to 5 wt. % of at least one of the elements tin, germanium or lead as promoters and at least one additional modifier metal. The additional modifier metal is an alkaline earth metal with a concentration by weight in the final catalyst of 0.01 to 20 wt. %.

DETAILED DESCRIPTION OF THE INVENTION

Surprisingly, it has been found that the catalyst stability can be essentially increased by exchanging the alkali metals exclusively used as modifiers in the prior art for at least one alkaline earth metal. Magnesium is preferably used as the alkaline earth metal. The catalyst optionally contains no alkali metal or indium.

The support for the catalysts according to the invention should have a pore volume of between 0.5 and 3 ml/g and a specific surface area, measured by nitrogen adsorption according to DIN (German Industrial Standard) 66 132, of at least 5 $m^2$/g. It must be sufficiently heat resistant under the conditions used for dehydrogenation. Any support materials which are already used in the prior art for dehydrogenation catalysts are suitable, such as for example activated carbon, silica, silicon carbide, clays and various silicates. Heat resistant inorganic oxides such as aluminum oxide, titanium dioxide, zirconium dioxide, chromium oxide and others, are especially suitable. Aluminum oxide from the transition series of crystallographic phases, such as for example η or γ-aluminum oxide, is preferably used as support.

The inert support may be moulded into spheres, pellets, extrudates or granules. Powdered material may also be used. Preferably, however, spheres of η or γ-aluminum oxide with diameters between 1 and 4 mm are used.

The bulk density of these spheres, due to the high porosity of the support, is less than 0.5 $g/cm^3$, preferably in the range between 0.25 and 0.4 $g/cm^3$. Below a bulk density of 0.25 $g/cm^3$ the supports are no longer sufficiently stable due to their high porosity. Above a bulk density of 0.4 $g/cm^3$, access by the reactants to the catalytically active components is impaired for the reactant molecules, due to the low porosity.

Suitable platinum group elements as the catalytically active component for the catalyst according to the invention are platinum, palladium, iridium, rhodium, osmium or ruthenium or mixtures thereof. Platinum is preferably used, however, as a platinum group element. The platinum group component is finely distributed within the entire catalyst. The proportion of platinum group component in the total weight of catalyst should be between 0.01 and about 5 wt. %. A concentration of platinum group component of 0.1 to 3 wt. % is preferably used.

The platinum group component may be introduced during production of the support by coprecipitation or cogelling. The platinum group component is preferably introduced, however, by impregnating the support material. For this, a solution or suspension of a decomposable precursor compound of the platinum group element is used. For example, in the case of platinum a solution of hexachloroplatinic acid, which can be further acidified with other acids in order to guarantee a homogeneous impregnation throughout the entire support particle, is suitable for this purpose. Other Pt salts such as, for example, tetraammineplatinum(II) nitrate, tetraammineplatinum(II) hydroxide and tetraammineplatinum(II) chloride are also suitable as platinum precursors.

The promoters used may be the elements tin, germanium or lead, separately or as a mixture. At least one of these elements is present. Tin is preferably used, however. Like the platinum group component, the promoter (e.g., tin component) is also distributed homogeneously over the catalyst particle. The proportion by weight of promoter (e.g., tin) in the final catalyst is 0.01 to about 5 wt. %, a concentration of 0.1 to 3 wt. % preferably being used.

The tin component may also be introduced during production of the support. Preferably, however, subsequent impregnation with a solution of tin chloride or another tin salt is also preferred here.

According to the present invention, the modifier metal used is at least one alkaline earth metal. The alkaline earth metal may also be introduced during production of the support. Subsequent introduction by impregnating with a soluble alkaline earth metal compound, however, is preferred. The proportion of alkaline earth metal in the total weight of final catalyst should be between 0.01 and 20 wt. %. A concentration of 0.1 to 10 wt. % of alkaline earth metal (e.g., magnesium) is preferably used.

The platinum group component, the promoter and the alkaline earth metal component may be introduced simultaneously or one after the other in any sequence by impregnating the support. It has proved particularly advantageous to deposit all the components in the catalyst onto the catalyst support or support material simultaneously from a common solution. To prepare the common impregnating solution, a tetraammine-platinum(II) salt is suitable as the precursor of, for example, platinum. When using hexachloroplatinic acid in the common impregnating solution, precipitation takes place after a short time, which can be inhibited only by means of strong acidification with inorganic acids such as hydrochloric acid or nitric acid. If a tetraamineplatinum(II) salt is used as the platinum precursor, then the common impregnating solution remains stable for a long time with the addition of only small amounts of acid.

Catalysts which are produced using one-stage impregnation are characterized by their catalytic activities, due to particularly good long-term stability. In addition, one-stage impregnation also represents an essential simplification in the method of production.

The catalyst may also contain indium as a further promoter. Indium, inter alia, has a positive effect on the long-term stability of the catalyst. It is preferably introduced as a soluble precursor together with the other components in the catalyst by impregnation in an amount of up to 5 wt. %, with respect to the total weight of final catalyst.

In addition to the components described above, the catalyst may also contain up to 5 wt. %, preferably up to 2 wt. %, of sulphur. The sulphur can be applied to the catalyst in any appropriate form. Suitable sources of sulphur are, for example, hydrogen sulphide and mercaptan compounds. Sulphur-containing compounds may also be introduced as sulphates, sulphites, sulphides or as an organic sulphur compound during production of the support. In the case of sulphur, however, it is also preferred that the support is coated with sulphur, together with the other components in the catalyst, from a common impregnating solution.

Long-term measurements using catalysts according to the present invention show that they surprisingly have better long-term stability than known catalysts, which can be attributed to the use of alkaline earth metals as modifiers. In addition to the alkaline earth metal component, the catalyst may also contain an alkali metal component with a proportion by weight in the final catalyst of 0.01 to 20 wt. %.

After applying the components to the support, the catalyst precursor obtained in this way is dried and calcined at temperatures between 300° and 700° C. for a period of 0.5 to 24 hours. Then the calcined catalyst is reduced by means of a gas phase reduction using an $H_2$-containing gas at temperatures between 200° and 700° C. The reduction conditions are selected so that the preponderant proportion of platinum group component is reduced to the metal. Reduction may take place either outside or inside the dehydrogenation reactor.

Dehydrogenation of normal paraffins is preferably performed in the gas phase. For this, the paraffins are heated to temperatures of between 300° and 900° C. before entering the catalyst zone and then passed over the catalyst at pressures between 0.08 and 10 MPa. The LHSV (LHSV= liquid hourly space velocity) is preferably between 0.1 and 100 $h^{-1}$. The product stream leaving the dehydrogenation zone contains mainly unconverted paraffins, hydrogen and monoolefins. The product stream is usually cooled. After separating a hydrogen-rich gas phase, a hydrocarbon-rich liquid phase is obtained. The liquid product mixture can be divided into a paraffin-rich and an olefin-rich fraction. The paraffin-rich fraction is usually passed through the dehydrogenation reactor again for further dehydrogenation, while the olefin-rich fraction is used to produce secondary and end products. Alternatively, the entire liquid product may be used for example to alkylate benzene. In this case, the olefins react with benzene to give linear alkylbenzene compounds which can easily be separated from unreactive paraffins. The paraffins are returned to the dehydrogenation reactor after separation. Any diolefins contained in the liquid product may be selectively hydrogenated to monoloefins between the dehydrogenation and alkylation reactors.

The following examples are intended to explain in more detail production of the catalyst according to the invention and its use for dehydrogenating linear paraffins:

Comparison Example 1

A conventional dehydrogenation catalyst A was prepared using lithium as modifier. The support was a spherical aluminum oxide with a bulk density of 0.3 $g/cm^3$ and a pore volume of 1.4 ml/g.

100 g of support were impregnated with 140 ml of an aqueous solution of 0.95 g of $SnCl_2 2H_2O$, 1.05 g of $In(NO_3)_3$ and 6.03 g of $LiNO_3$. The solution also contained 1.2 wt. % of $HNO_3$. After impregnation, the support was dried and calcined at 550° C. for a period of 1.5 hours. Then the support was impregnated with 140 ml of an aqueous solution which contained 0.4 g of Pt in the form of $H_2PtCl_6$ and 1.2 wt. % of $HNO_3$. The catalyst precursor obtained in this way was again dried and calcined in the same way as described above. Then the catalyst was reduced at 490° C. in a stream of forming gas (5 vol. % of $H_2$; 95 vol. % of $N_2$). The final catalyst contained 0.4 wt. % of platinum, 0.5 wt. % of tin, 0.4 wt. % of indium and 0.6 wt. % of lithium.

This catalyst, and also the catalysts in the following examples, were used to dehydrogenate a $C_{10}$–$C_{14}$ paraffin mixture. For this, 10 ml of the respective catalyst were placed in a reactor, through which was passed a gas mixture consisting of hydrogen and paraffins at a pressure of 2.3 bar with an LHSV of 22 $h^{-1}$. The ratio $H_2$/paraffin was 4.7 mol/mol. The initial temperature in the catalyst bed was selected so that an olefin content of about 11 wt.% was achieved in the liquid product. This was the case at a temperature of 453° C. Since the catalyst deactivated, the temperature had to be raised at regular intervals during the course of the test. After 7.5 days a catalyst temperature of 490° C. was reached. The average olefin content of the liquid product was 11.2 wt. % in this test.

EXAMPLE 1

Catalyst B according to the present invention was prepared in the same way as the conventional catalyst A. $LiNO_3$ was replaced, however, with the corresponding amount of Mg(NO$_3$)$_2$6H$_2$O. The final catalyst contained 0.4 wt. % of platinum, 0.5 wt. % of tin, 0.4 wt. % of indium and 2.1 wt. % of magnesium.

This catalyst was also used to dehydrogenate a C$_{10}$–C$_{14}$ paraffin mixture, like the catalyst in comparison example 1. The average olefin content in this test was 11.8 wt. %. The final temperature of 490° C. was achieved only after 10 days. Catalyst B is therefore unexpectedly much more stable than conventional catalyst A. With catalyst B the useful lifetime was increased by one third, although the average concentration of olefin was about 0.6 wt. % higher than with catalyst A.

EXAMPLE 2

A catalyst C according to the invention was prepared in a one-stage process by simultaneous application to the catalyst support of all the catalyst components from a common solution.

In this case, 100 g of support material from comparison example 1 were impregnated with 140 ml of an aqueous solution of 0.79 g of Pt(NH$_3$)$_4$(NO$_3$)$_2$, 22.39 g of Mg(NO$_3$)$_2$6H$_2$O, 1.05 g of In(NO$_3$)$_3$ and 0.95 g of SnCl$_2$2H$_2$O. The solution also contained 1.2 wt. % of HNO$_3$. The catalyst precursor was dried, calcined and reduced as described in comparison example 1. This catalyst C, prepared by one-stage impregnation, had exceptional long-term stability. The end temperature of 490° C. was only reached after 22 days.

EXAMPLE 3

A further catalyst D according to the present invention was prepared in the same way as in example 2, but without indium, and used for the dehydrogenation of C$_{10}$–C$_{14}$-paraffins. The average olefin content in this test was 10.9 wt. %. A catalyst temperature of 490° C. was reached after 16 days. Although this catalyst contained no indium, it provided larger amounts of olefin than conventional catalyst A with indium.

Comparison Example 2

A comparison catalyst E was prepared based on an aluminum oxide support which had a bulk density of 0.6 g/cm$^3$ and a pore volume of 0.64 ml/g. 100 g of this support were impregnated with 0.3 g of Pt(NH$_3$)$_4$(NO$_3$)$_2$, 0.47 g of In(NO$_3$)$_3$, 22.38 g of Mg(NO$_3$)$_2$6H$_2$O and 0.43 g of SnCl$_2$2H$_2$O, dissolved in 64 ml of a 1.2 wt. % HNO$_3$ solution, dried, calcined and reduced at 490° C. The metal contents were: 0.18 wt. % Pt, 0.18 wt. %, 0.23 wt. % Sn and 2.1 wt. % Mg.

10 ml (5.93 g) of this catalyst were tested for dehydrogenation in precisely the same way as described-in comparison example 1. The lower Pt content of the catalyst as compared with the other examples was precisely compensated for by its higher bulk density. Accordingly, the amount of catalytically active platinum in each of the application examples listed here was identical.

With an initial temperature of 462° C., the olefin content in the product stream was clearly too low, being only 4.9 wt. %, and an increase of temperature to 481° C. did not produce any improvement. The poor results for this catalyst are attributed to its low porosity which makes access by the reactants to the catalytically active components difficult.

The data from the above examples are summarized in the following table:

|  | day when catalyst temperature reached 490° C. | average olefin content |
| --- | --- | --- |
| Comp. Ex. 1 | 7.5 | 11.2 wt. % |
| Example 1 | 10 | 11.8 wt. % |
| Example 2 | 22 | — |
| Example 3 | 16 | 10.9 wt. % |

Thus, the data shows that with catalysts produced in accordance with the present invention which contain an alkaline earth metal possess unexpectedly superior characteristics with regards to stability in comparison to comparative example 1 which has no alkaline earth metal.

Further variations and modifications of the foregoing will be apparent to those skilled in the art and such variations and modifications are intended to be encompassed by the claims that are appended hereto.

German Priority Application P 44 42 327.6, filed on 29 Nov. 1994, is relied on and incorporated by reference in its entirety.

We claim:

1. A catalyst for the dehydrogenation of C$_6$–C$_{15}$ paraffins, said catalyst comprising on an inorganic support 0.01 to 5 wt. % of at least one platinum group metal, 0.01 to 5 wt. % of at least one promoter selected from the group consisting of tin, germanium and lead, and magnesium as a modifier with a concentration by weight in the final catalyst of 0.01 to 20 wt. % wherein said support has a bulk density of 0.25 to less than 0.5 g/cm$^3$.

2. The catalyst according to one of claim 1, wherein said platinum group metal is platinum.

3. The catalyst according to claim 1, wherein said promoter is tin.

4. The catalyst according to claim 1, wherein said catalyst further comprises up to 5 wt. % of indium.

5. The catalyst according to claim 1, wherein said catalyst further comprises up to 5 wt. % of sulphur.

6. The catalyst according to claim 1, wherein said catalyst further comprises up to 2 wt. % of sulphur.

7. The catalyst according to claim 1, wherein said at least one platinum group metal is present in an amount of 0.01 to 3 wt. %.

8. The catalyst according to claim 1, wherein said promoter is present in an amount of 0.01 to 3 wt. %.

9. The catalyst according to claim 1, wherein said at least one alkaline earth metal is present in an amount of 0.01 to 10 wt. %.

10. The catalyst according to claim 1, wherein said catalyst further comprises 0.1 to 20 wt. % of at least one alkali metal.

11. The catalyst according to claim 1, wherein said support has a pore volume of 0.5 to 3 ml/g.

12. The catalyst according to claim 1, wherein said support has a specific surface area of at least 5 m$^2$/g.

13. The catalyst according to claim 1, wherein said support comprises aluminum oxide from the transition series.

14. The catalyst according to claim 13, wherein said support is η or γ-aluminum oxide.

15. The catalyst according to claim 1, wherein said support has a bulk density of 0.25 to 0.4 g/cm$_3$.

16. A catalyst for the dehydrogenation of C$_6$–C$_{15}$ paraffins comprising, on an inorganic support, 0.01 to 5 wt. % of at least one platinum group metal, 0.01 to 5 wt. % of at least one of the elements tin, germanium and lead as a promoter and magnesium as a modifier, obtained by simultaneous introduction to the inorganic support of a soluble precursor of said platinum group metal, said promoter and said modifier from a common impregnation solution to thereby form an impregnated support, drying of the impregnated support, calcining said support at a temperature between 300° C. and 700° C. and subsequent reduction of said precursor in a hydrogen-containing gas at temperatures between 200° C. and 700° C., wherein said magnesium is present at a concentration by weight of 0.01 to 20 wt. % of the final catalyst.

17. The catalyst according to claim 16, further comprising up to 5 wt. % of indium as a promoter.

18. The catalyst according to claim 16, further comprising up to 5 wt. % of sulphur applied to the support material together with the other components from the common impregnating solution.

19. A process for preparing a catalyst for the dehydrogenation of $C_6$–$C_{15}$ paraffins, containing, on an inorganic support, 0.01 to 5 wt. % of at least one platinum group metal, 0.01 to 5 wt. % of at least one of the elements tin, germanium and lead as promoter and magnesium as a modifier, comprising simultaneously applying to the support a soluble precursor of the platinum group metal, promoter and modifier from a common impregnation solution, drying the support, calcining said support at temperatures between 300° and 700° C. and then reducing said precursor in a hydrogen-containing gas at temperatures between 200° and 700° C., wherein magnesium is at a concentration of 0.01 to 20 wt. % of the final catalyst as modifier and wherein said support has a bulk density of 0.25 to less than 0.5 g/cm$^3$.

20. The process according to claim 19, further comprising adding a soluble precursor of indium.

21. The process according to claim 19, further comprising adding a soluble precursor of sulphur.

* * * * *